(12) United States Patent
Ferguson

(10) Patent No.: US 7,815,681 B2
(45) Date of Patent: Oct. 19, 2010

(54) ORTHOPEDIC SUPPORT LOCATING OR CENTERING FEATURE AND METHOD

(75) Inventor: Joe Ferguson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 486 days.

(21) Appl. No.: 11/414,831

(22) Filed: Apr. 28, 2006

(65) Prior Publication Data

US 2007/0270965 A1    Nov. 22, 2007

(51) Int. Cl.
*A61F 2/44* (2006.01)
(52) U.S. Cl. ..................... 623/17.16; 606/71
(58) Field of Classification Search ................ 606/280, 606/71; 623/17.11, 17.15, 17.16
See application file for complete search history.

(56) References Cited

U.S. PATENT DOCUMENTS

| | | | |
|---|---|---|---|
| 4,599,086 A * | 7/1986 | Doty | 606/86 A |
| 5,888,223 A * | 3/1999 | Bray, Jr. | 623/17.16 |
| 6,471,724 B2 | 10/2002 | Zdeblick | |
| 6,648,891 B2 | 11/2003 | Kim | |
| 6,663,637 B2 | 12/2003 | Dixon | |
| 6,849,093 B2 * | 2/2005 | Michelson | 623/17.15 |
| 2004/0034430 A1 | 2/2004 | Falahee | |
| 2004/0039387 A1 | 2/2004 | Gause | |
| 2004/0193269 A1* | 9/2004 | Fraser et al. | 623/17.11 |
| 2004/0215203 A1 | 10/2004 | Michelson | |
| 2005/0027300 A1 | 2/2005 | Hawkins | |
| 2005/0101960 A1* | 5/2005 | Fiere et al. | 606/72 |
| 2006/0149378 A1* | 7/2006 | Chase et al. | 623/17.11 |

\* cited by examiner

*Primary Examiner*—Eduardo C Robert
*Assistant Examiner*—Elana B Fisher

(57) ABSTRACT

Spinal plate positioning system including a spinal plate, centering member and implant, is used to position and center a spinal plate over an implant in an intervertebral space. Implant may include a centering feature which may engage a surface of centering member or spinal plate to aid in placement of spinal plate.

20 Claims, 4 Drawing Sheets

ORTHOPEDIC SUPPORT LOCATING OR CENTERING FEATURE AND METHOD

This disclosure generally concerns improved orthopedic implants and plates which form a fixation apparatus. In particular, it concerns implants incorporating a feature which aids in the placement of a plate.

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease, aging, or other factors. Disruption of the annulus fibrosus allows the nucleus pulposus to protrude into the vertebral canal, a condition commonly referred to as a herniated or ruptured disc. The extruded nucleus pulposus can press on a spinal nerve, which may result in nerve damage, pain, numbness, muscle weakness and paralysis. Intervertebral discs may also deteriorate due to the normal aging process or disease. As a disc dehydrates and hardens, the disc space height may be reduced which could lead to instability of the spine, decreased mobility and pain.

In certain instances of disc rupture or other injury or deformity, a partial discectomy with insertion of a spacer, prosthesis or other type of implant and/or fusion of the adjacent vertebrae can be performed. Synthetic, naturally-derived and composite implants have been used in the intervertebral space to prevent disc space collapse and/or promote fusion of the adjacent vertebrae across the disc space. A plate may be placed over the implant and attached to the adjacent vertebrae to provide additional stability directly to the vertebrae, to prevent migration of the implant, or for other reasons. In practice, given the vagaries of anatomy, obscuring of the surgical site by tissue or bodily fluids, or for other reasons, it can be difficult to properly position or center a plate over an implant.

SUMMARY

In certain embodiments, a spinal plate centering system for centering a spinal plate across a disc space is disclosed, including a centering member having spaced apart first and second surfaces defining a centering member periphery and a centering member thickness. The first surface has at least one protrusion adapted to engage an implant disposed in the disc space, and at least a portion of the centering member periphery is adapted to engage the spinal plate. A handle may be provided coupled to the centering member and extending generally orthogonal to the second surface. The at least one protrusion may be adapted to engage a recess in the implant, and the centering member periphery may have substantially a same shape as an opening in the spinal plate, which opening may be centrally-disposed. The centering member thickness may generally correspond to a spinal plate thickness. Further, the engagement between the spinal plate and the centering member periphery may be a frictional engagement sufficient to provide movement of the spinal plate coincident with movement of the centering member. In particular embodiments, the centering member first surface may include two spaced apart protrusions adapted to engage at least one recess in the implant, and the implant may include at least two recesses, each of the recesses adapted to receive one of the spaced apart protrusions.

In other embodiments, a method of centering a spinal plate across a disc space is provided, which includes inserting an implant into the disc space, engaging the spinal plate with a centering member that has first and second spaced apart surfaces defining a centering member periphery, positioning the centering member over the implant and engaging the implant with the centering member, coupling the spinal plate to at least one vertebral body adjacent the disc space, and disengaging the centering member from the spinal plate. Methods may also include those in which the centering member includes means for engaging the implant, the engaging means adapted to align the centering member with the implant, or in which the implant includes at least one recess adapted to receive a protrusion from the centering member first surface. Engaging the spinal plate with the centering member can include frictionally engaging an opening in the spinal plate with the centering member, and positioning the centering member over the implant can operate to position the spinal plate over the implant. The implant may have a centering mark visible when the implant is disposed in the disc space, and methods may include visually aligning the centering member with the centering mark prior to engaging the implant with the centering member. A centering mark may include an etched mark disposed in a surface of the implant.

In another embodiment, a system for centering a spinal plate across a disc space is provided, which includes an implant adapted to be disposed in the disc space that includes a centering mark on an implant surface, a centering member with spaced apart first and second surfaces defining a centering member periphery and a centering member thickness and at least a portion of the centering member periphery is adapted to frictionally engage the spinal plate, and means for removably coupling the implant and centering member in a desired orientation. The means for removably coupling the implant and centering member can include at least one protrusion disposed on the first surface and at least one recess disposed on the implant surface, and/or at least one recess disposed on the first surface and at least one protrusion disposed on the implant surface. The plate may include an opening adapted to frictionally engage at least a portion of the centering member periphery.

DESCRIPTION OF THE ILLUSTRATED EMBODIMENT

Figure 1:
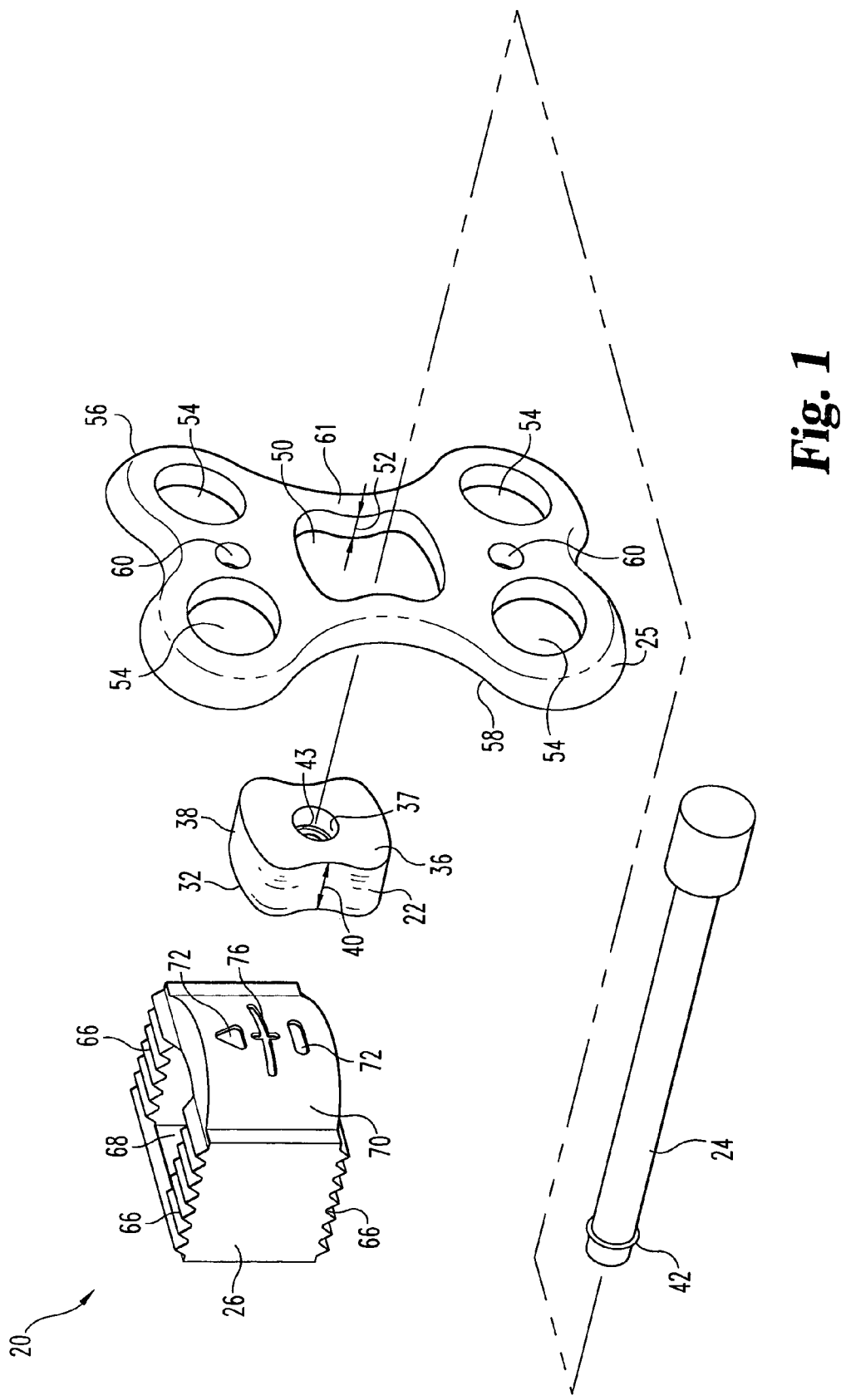
FIG. 1 is an exploded perspective view of an embodiment of an orthopedic plate placement system.
Figure 2:
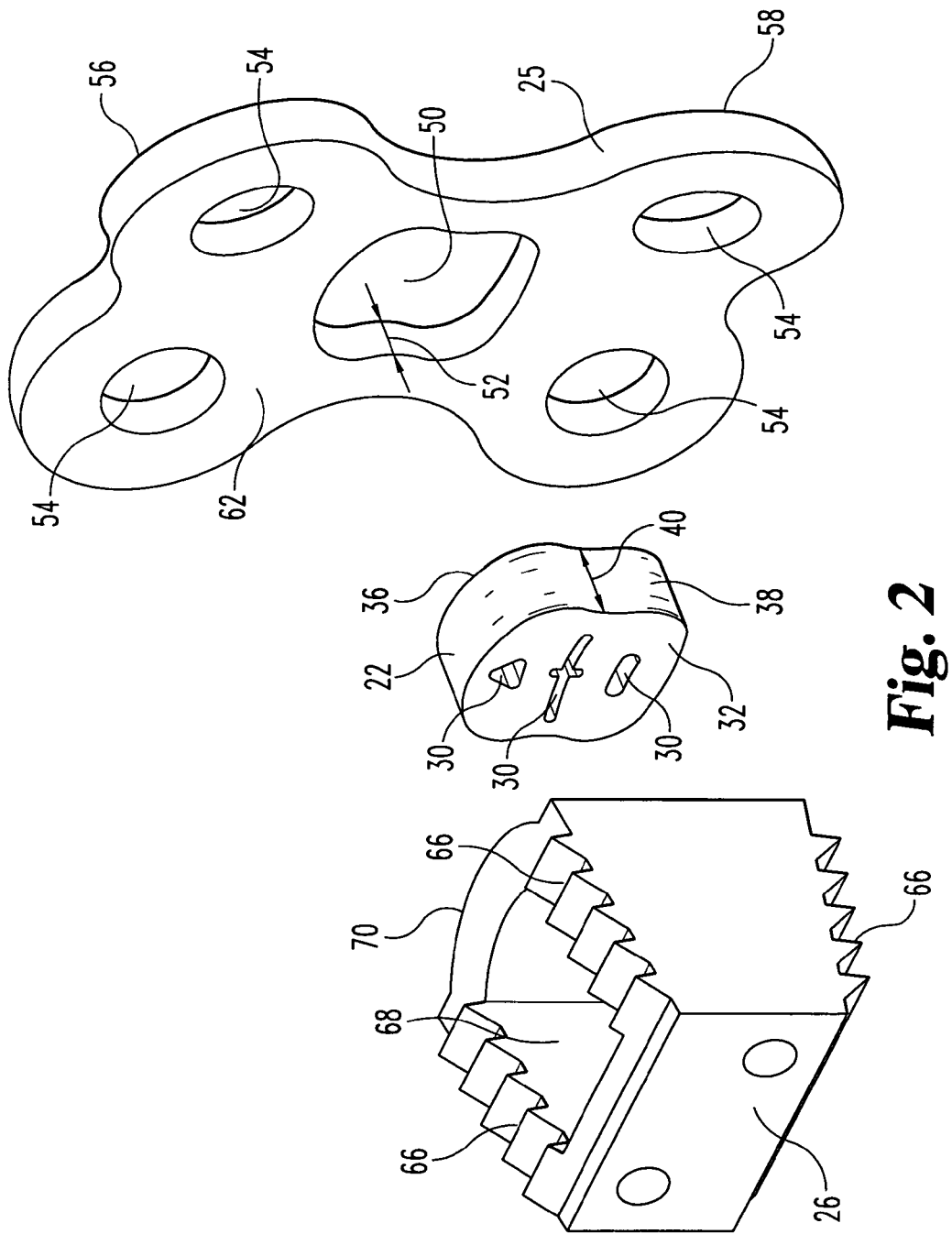
FIG. 2 is an exploded perspective view of aspects of the system shown in FIG. 1 from a different angle.
Figure 3:
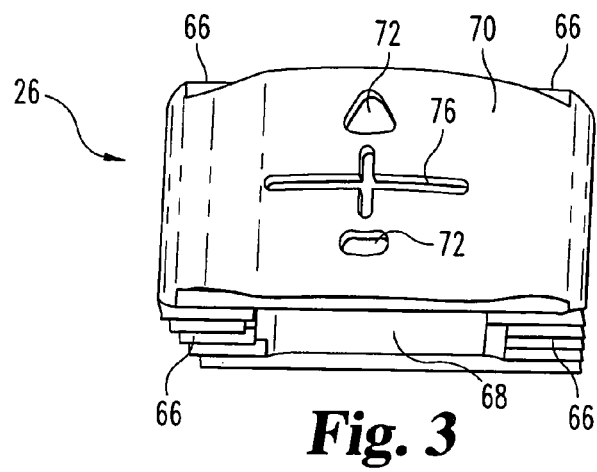
FIG. 3 is a front view in perspective of an embodiment of an intervertebral implant.
Figure 4:
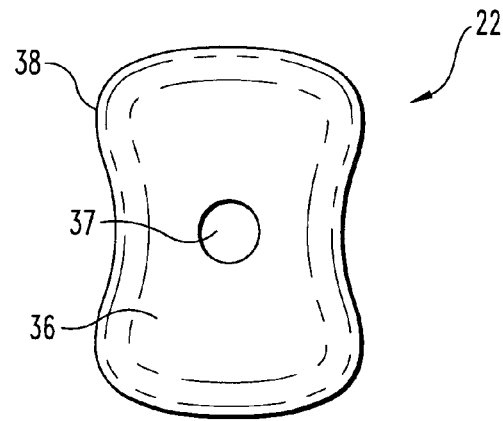
FIG. 4 is a front view of an embodiment of a centering piece shown in FIG. 1.
Figure 5:
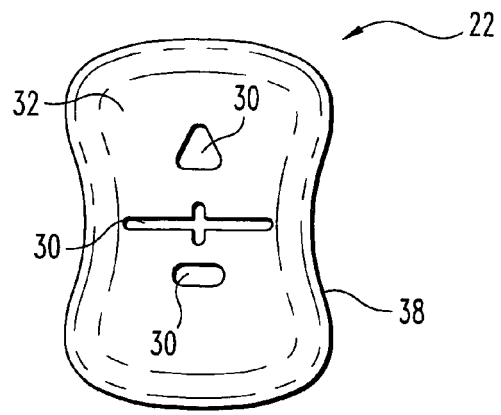
FIG. 5 is a rear view of an embodiment of a centering piece shown in FIG. 1.
Figure 6:
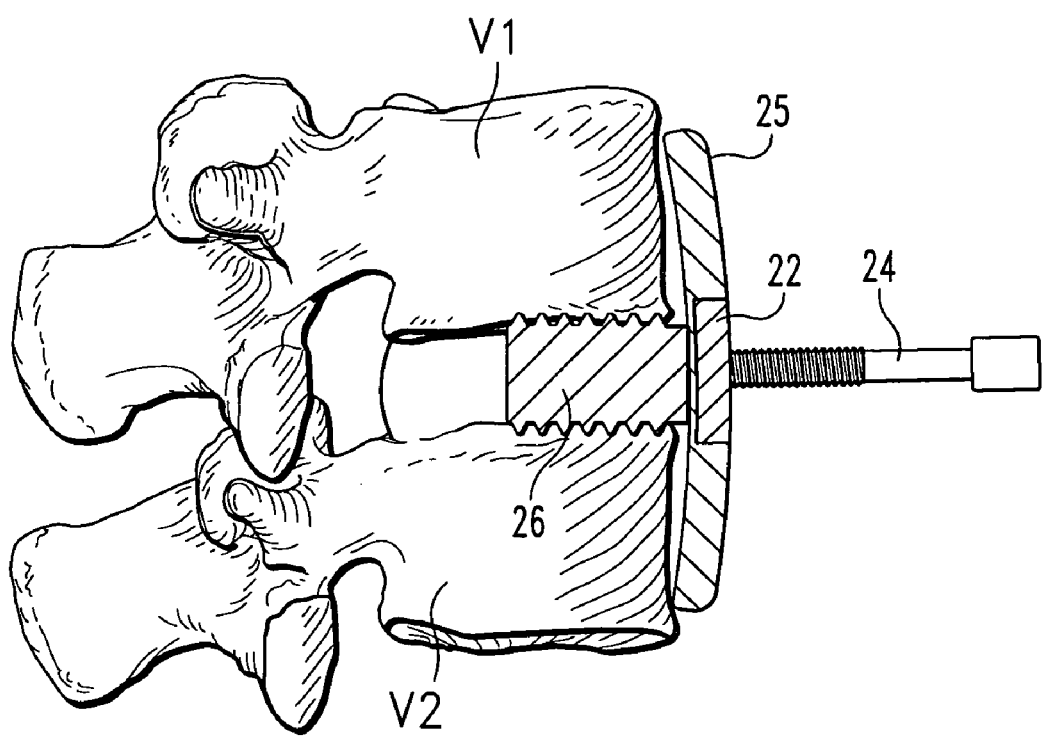
FIG. 6 is a partial cross-sectional view from the side of the embodiment of the system shown in FIG. 1 in relation to vertebrae.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein being contemplated as would normally occur to one skilled in the art to which the disclosure relates.

Referring generally to the figures, there is shown an embodiment of a spinal plate centering system 20. In the illustrated embodiment, system 20 includes centering member 22 and handle 24, which are engageable to spinal plate 25, and implant 26. Generally, as further discussed below, centering member 22 assists in placing plate 25 with respect to implant 26 in a desirable location on bone adjacent implant 26. The context of the discussion that follows is spinal surgery, although it will be seen that the devices and methods disclosed herein could be used in other contexts as well.

Centering member 22, in the illustrated embodiment, includes at least one implant engaging feature in the form of protrusions 30 on a first surface 32, and a second surface 36 spaced apart from surface 32 and having an aperture 37. Surfaces 32 and 36 define a periphery 38 and thickness 40 of centering member 22. Centering member 22 is shown as being generally a generally rectangular solid with concave sides, though other regular or irregular shapes, such as cylindrical or polygonal, could be used. At least a portion of periphery 38 of member 22 may be adapted to engage spinal plate 25, and in the illustrated embodiment all or substantially all of periphery 38 engages or is adjacent to a portion of plate 25. Aperture 37 on surface 36 may be generally configured to receive a portion of handle 24. In the illustrated embodiment, handle 24 includes a ridge 42 that extends partially or completely around the perimeter of handle 24, and aperture 37 includes a groove 43 that extends partially or completely around the perimeter of aperture 37. Accordingly, handle 24 may be inserted into aperture 37 so that ridge 42 fits into groove 43. In other embodiments, handle 24 may be integral with member 22, may have a bayonet-type connection with member 22, or may be otherwise connected or positioned with respect to member 22. Handle 24 can be orthogonal or otherwise angled with respect to at least one surface of member 22, or where member 22 is substantially planar, with respect to member 22.

As previously noted, surface 32 may be adapted to engage implant 26. In the illustrated embodiment, surface 32 includes protrusions 30. In a particular embodiment, one protrusion 30 is substantially triangular, one is substantially linear, and one is substantially cross-shaped. The illustrated embodiment shows protrusions 30 being substantially vertically aligned. It will be seen that one such protrusion may be sufficient to removably connect member 22 and implant 26. In other embodiments, one or more recesses or other keying structures could be included along with or instead of one or more protrusions 30. Protrusions 30 could be configured differently in shape, size and/or location to allow for ease of mating and centering specificity. Surface 32 or other parts of member 22 could also have other ways for engaging implant 26. For example, surface 32 could engage implant 26 in such a way that physically corresponding mated parts would not be required, such as through magnetic or chemical engagement. Thickness 40 of member 22 may be substantially uniform, as in the illustrated embodiment, or may be non-uniform or variable. Further, the illustrated embodiment of member 22 has thickness 40 that is approximately that of plate 25. Thickness 40 might also be greater or smaller than that of plate 25. Variations in thickness 40 might also occur throughout centering member 24. For example, member 22 could have a greater thickness at or near a center portion, and smaller thickness at the periphery 38. Likewise, member 22 could have a greater thickness at or near periphery 38 and a smaller thickness at or near a center portion.

Plate 25 may be any of a variety usable for support or stabilization of vertebrae or vertebral motion segments. In the illustrated embodiment, plate 25 is generally rectangular and has a centrally-located opening, 50, a thickness 52, and four holes 54 for bone anchors (not shown) such as screws. Among other things, opening 50 is for accommodating all or part of periphery 38 of member 22, as further described below, and is thus substantially rectangular in shape with pinched or concave sides (i.e. a concave side opening defined by convex walls). Two holes 54 are located on a relatively upper portion 56 and two holes 54 are located on a relatively lower portion 58 of plate 25. Additionally, the illustrated embodiment of plate 25 includes two retaining member apertures 60, each situated between pairs of holes 54, and a relatively outer side 61 that is at least slightly convex and relatively inner side 62 that is at least slightly concave. Such curvature may approximate the natural curvature of vertebrae and/or the spinal area into which plate 25 is to be inserted. Thickness 52 of plate 22 may be relatively constant or uniform, as in the illustrated embodiment, or may be variable.

In the illustrated embodiment, opening 50 is substantially rectangular and centrally located in plate 25. Opening 50 is of substantially the same shape and size as member 22, described above, but may be of any shape and size which allows member 22 to be at least partially inserted. For example, opening 50 could be larger or smaller than depicted in the illustration and could be round, oval, square, triangular or otherwise shaped. Opening 50 may have additional features to enhance interaction with centering member 24, such as roughened sides and a configuration mated or partially mated to periphery 38 of member 24.

Plate 25 may also have other features. For example, plate 25 could be configured to allow for adjustment, such as by having at least two separate sections which slidably engage one another. Plate 25 could also be rigid or flexible and may be anatomically contoured. The illustrated embodiment depicts plate 25 generally used in single level (involving two vertebrae and one disc space) implantation, though embodiments of plates applicable to multiple level implantation could also be used. Additionally, plate 25 can include screws (not shown) or other structure for blocking or retaining bone anchors in holes 54 of plate 25. Such screws can be inserted in apertures 60 so that a portion of them cover portions of anchors through holes 54.

Implant 26 may be any of a variety of devices, and in the illustrated embodiment is a block-type spacer implant having upper and lower ridges 66 intended to contact vertebral endplates or adjacent tissue. Implant 26 may be shaped to generally fit at least a part of an intervertebral space, or may be otherwise shaped. In the illustrated embodiment, implant 26 includes a central opening 68 and a front surface 70. Implant 26 may be of metal, synthetic materials, natural materials such as graft, or a combination of these materials. Growth factors, graft material, osteoinductive compositions and/or other materials might be incorporated in or coated on the implant 26 and/or placed in opening 68. Implant 26 is generally load-bearing in the illustrated embodiment, while in other cases a non load-bearing implant could be used.

Surface 70 includes one or more plate centering features in the form of recesses 72, and groove or mark 76 generally centered on surface 70. Such features may be visual, physical or otherwise configured, and are compatible with the features described above with respect to member 22. In the illustrated embodiment, one recess 72 is substantially triangular in shape, and another recess 72 is substantially linear or oval in shape, so as to be compatible with protrusions 30 of member 22 described above. Mark 76, in the illustrated embodiment, is a cross-shaped groove or relief that is compatible with cross-shaped protrusion 30 of member 22 and thus may be considered a physical centering feature. Mark 76 may also be a visual centering feature due to its visual characteristics, or in other embodiments may be solely visual, having little or no depth or height, such as one or more machined, etched, laser-marked or other equivalent line(s), design(s), or other useful visual indications. Mark 76 may be centered on implant surface 70 or may be offset. Mark 76 might take the form of an outline of member 22, such that centering or proper location is achieved when member 22 is placed on surface 70 within the boundaries of mark 76. It will be seen that a single recess or other centering or locating features could be included on implant 26, or multiple such features could be included, and in certain embodiments at least as many recesses or other features are provided on implant 26 as there are protrusions or other features provided on member 22. The illustrated embodiment of implant 26 is shown having both physical and visual centering features (recesses 72 and mark 76), although in other embodiments one or the other may be provided. Implant 26 could also have other plate centering features, for example, those that would allow for magnetic or chemical engagement.

The apparatus disclosed herein may be used in at least the following manner. First, a surgeon may access an appropriate area of the spine of the patient via an open, minimally-invasive or other approach. An intervertebral disc may then be resected, a discectomy performed or other procedure to prepare an intervertebral space. Adjacent vertebrae V1 and V2 can be distracted using a distraction tool (not shown) so that implant 26 may be placed within a disc space. With certain embodiments of implant 26, separate distraction may not be needed, insofar as pressing implant 26 against vertebrae may separate the vertebrae to enable insertion of implant 26 into a disc space. After implant 26 has been placed, member 22 may be engaged to plate 25 or implant 26. In the former case, where member 22 is engaged to plate 25, member 22 can be inserted into opening 50 of plate 25. In some embodiments, periphery 38 of member 22 may frictionally engage plate 25 within opening 50, or member 22 may be relatively loosely engaged or connected to plate 25 in another fashion. Member 22 may then be positioned over implant 26. In embodiments in which a handle (e.g. handle 24) can be used with member 22, such a handle may be connected to member 22 (if not integral with it) and used to move member 22 and plate 25 to a position adjacent implant 26. Alternatively, member 22 may be first engaged to implant 26, as described below, and plate 25 may then be placed over member 22.

The surgeon can rely on visual centering feature(s) (if present) such as mark 56 on implant 26 to initially guide the placement of member 22. Additionally, if such visual centering feature(s) are such that member 22 does not wholly obscure them, such feature(s) may be used through the placement. When member 22 is adjacent implant 26, protrusions 30 on member 22 are engaged and/or mated with recesses 72 of implant 26. Using the particular illustrated embodiment as an example, triangular protrusion 30 is inserted into triangular recess 72, linear or oval protrusion 30 is inserted into linear or oval recess 72, and cross-shaped protrusion 30 is inserted into or placed against mark 76. Plate 25 may then be coupled to at least one of the adjacent vertebral bodies. Attachment of the plate 22 to the vertebrae may be accomplished by drilling into the vertebrae through holes 64 and threading bone screws (not shown) or otherwise placing bone anchors through holes 64 and into the bone tissue, thereby fixing plate 25. As suggested above, locking or retaining mechanism(s) such as set screws may be installed in or on plate 25 over the bone screws. When plate 25 is attached to one or both of the vertebrae, member 22 may be disengaged from implant 26, withdrawn through plate 25 and removed from the surgical site. Additional procedures may be performed prior to, during, or after placement of implant 26, member 22 and/or plate 25, including placement of other implants, compression, rotation, distraction or other manipulation of vertebrae, or other procedures.

Other embodiments of the use of the above identified apparatus are possible. For example, where implant 26 includes one or more visual or physical features, member 22 may not be necessary for proper centering or other location of plate 25. In the absence of member 22, in this example, one or more visual feature(s) (e.g. mark 76) or one or more physical features (e.g. recesses 72) on implant 26 could be viewed or otherwise aligned through opening 50 of plate 25. When plate 25 is adjacent the vertebrae and properly oriented with respect to implant 26, plate 25 can be attached to the vertebrae. Additionally, physical centering features on implant 26 could mate with physical features on plate 25, such as protrusions like those described above with respect to member 22.

The illustrated embodiments of devices and methods are useful in the cervical and other regions of the spine. They may also be used in devices intended for other orthopedic locations as well.

The apparatus described above may be made of suitable biocompatible materials. Implant 26, for example, may be made partially or wholly of natural tissues, synthetic materials such as particulate mineral material like calcium phosphate ceramic, synthetic collagens, or polymers like polyetheretherketone (PEEK), or metals like titanium or stainless steel. Plate 25 could be manufactured of similar materials, and in certain embodiments plate 25 may be made of the same material as implant 26. Member 22 may be made of relatively rigid or somewhat flexible or compressible material that is compatible with fitting in opening 50 of plate 25 and recesses 72 and/or mark 76 of implant 26, in the embodiments described above.

It will be noted that the illustrated embodiment shows substantially the entire periphery 38 of member 22 engaging opening 50 of plate 25. Member 22 may be constructed so that only a portion of periphery 38 contacts plate 25. For example, member 22 could be cross or X-shaped, such that the tips of the cross or X engage plate 25 other embodiments of periphery 38 might engage plate 25 with three or fewer points, or otherwise with a relatively small portion of total periphery 38. As discussed above with respect to member 22 generally, periphery 38 could be substantially rigid, or could have a compressible, malleable or otherwise variable shape or configuration.

The attachment of plate 25 to vertebrae has been primarily described through use of bone screws fixing the components to the vertebra. It is understood that alternative attachment anchors, structures or methods may be used, such as by stapling, adhesive connection, clamping, or hooking.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected.

I claim:

1. A spinal plate centering system comprising:
   a spinal plate for extending across a disc space and having a plurality of holes;
   an implant for insertion in a disc space;
   a centering member comprising:
      spaced apart first and second surfaces defining a centering member periphery having a concave portion and a centering member thickness;
      the first surface comprising at least one non-threaded protrusion adapted to engage the implant when the implant is disposed in the disc space; and
      wherein at least a portion of the centering member periphery is adapted to fit within an opening in the spinal plate so that said centering member is non-rotatable with respect to the spinal plate when within the opening of the spinal plate.

2. The spinal plate centering system as in claim 1 further comprising a handle coupled to the centering member and extending generally orthogonal to the second surface.

3. The system as in claim 2, wherein said handle is able to turn with respect to said centering member.

4. The spinal plate centering system as in claim 1 wherein the at least one protrusion is adapted to engage a recess in the implant.

5. The spinal plate centering system as in claim 1 wherein the centering member periphery has substantially a same shape as an opening in the spinal plate.

6. The spinal plate centering system as in claim 5 wherein the opening is centrally-disposed in the spinal plate.

7. The spinal plate centering system as in claim 1 wherein the centering member thickness generally corresponds to a spinal plate thickness.

8. The spinal plate centering system as in claim 1 wherein the centering member periphery is configured to have a frictional engagement with the spinal plate sufficient to provide movement of the spinal plate coincident with movement of the centering member.

9. The spinal plate centering system as in claim 1 wherein the centering member first surface comprises two spaced apart protrusions adapted to engage at least one recess in the implant.

10. The spinal plate centering system as in claim 9 wherein the implant comprises at least two recesses, each of the recesses adapted to receive one of the spaced apart protrusions.

11. The system as in claim 1, further comprising a handle having a longitudinal axis and being connected to said centering member, wherein said centering member periphery is an edge surface between said first and second surfaces, and said second surface contacts said handle, and said first surface is substantially parallel to said second surface and facing away from said handle along said axis.

12. The system as in claim 1, wherein said at least one protrusion includes a first protrusion having a first shape and a second protrusion having a second shape, said first shape being different from said second shape.

13. The system as in claim 1, wherein said centering member has a top, a bottom and two sides, said top, bottom and sides facing the spinal plate when said centering member engages the spinal plate, and wherein the distance between said top and said bottom is different from the distance between said two sides.

14. The spinal plate centering system of claim 1, wherein said at least one protrusion has a shape from the group consisting of: cross-shaped, triangle-shaped and linear.

15. The spinal plate centering system of claim 1, wherein said at least one protrusion is off-center with respect to said centering member.

16. A system comprising:
    an implant adapted to be disposed in a spinal disc space, the implant comprising a centering mark on an implant surface;
    a spinal plate for placement across the disc space;
    a centering member comprising:
       spaced apart first and second surfaces defining a centering member periphery that is non-circular and a centering member thickness;
       wherein at least a portion of the centering member periphery is adapted to frictionally engage the spinal plate within an opening in the plate, so that the centering member is limited in rotation with respect to said plate; and
    means for removably coupling the implant and centering member in a desired orientation.

17. The system as in claim 16 wherein the means for removably coupling the implant and centering member comprises at least one protrusion disposed on the first surface and at least one recess disposed on the implant surface.

18. The system as in claim 16 wherein the means for removably coupling the implant and centering member comprises at least one recess disposed on the first surface and at least one protrusion disposed on the implant surface.

19. The system as in claim 16 wherein the spinal plate comprises an opening adapted to frictionally engage at least a portion of the centering member periphery.

20. An orthopedic apparatus for supporting first and second vertebrae having a disc space between them, comprising:
    an intervertebral implant adapted to be placed within the disc space, said implant having an external surface with at least one recess, said external surface adapted to face out from the disc space when implanted;
    a centering member having an inner surface, an outer surface, and a peripheral surface separating said inner and outer surfaces, said inner surface having at least one protrusion extending therefrom that is adapted to be inserted into said at least one recess so as to maintain said centering member in a desired orientation with respect to said implant, said outer surface including an opening, and said peripheral surface having a concave portion;
    a plate member having at least first and second holes for bone screws and an opening sized and configured to accommodate said centering member, wherein when said centering member is within said opening of said plate member and said protrusion of said centering member is within said recess of said implant, said first hole of said plate member is adjacent the first vertebra so that a bone screw may be inserted through said first hole and into the first vertebra and said second hole of said plate member is adjacent the second vertebra so that a bone screw may be inserted through said second hole and into the second vertebra.

* * * * *